United States Patent
Sandrin et al.

(10) Patent No.: US 7,578,789 B2
(45) Date of Patent: Aug. 25, 2009

(54) DEVICE AND METHOD FOR MEASURING THE ELASTICITY OF A HUMAN OR ANIMAL ORGAN

(75) Inventors: Laurent Sandrin, L'Hay-les-Roses (FR); Jean-Michel Hasquenoph, Couilly-Pont-aux-Dames (FR)

(73) Assignee: Echosens (FR)

( * ) Notice: Subject to any disclaimer, the term of this patent is extended or adjusted under 35 U.S.C. 154(b) by 804 days.

(21) Appl. No.: 11/049,400

(22) Filed: Feb. 2, 2005

(65) Prior Publication Data

US 2005/0203398 A1  Sep. 15, 2005

Related U.S. Application Data

(63) Continuation of application No. PCT/FR03/02243, filed on Jul. 16, 2003.

(30) Foreign Application Priority Data

Aug. 8, 2002 (FR) .................................. 02 10104

(51) Int. Cl.
*A61B 8/00* (2006.01)
(52) U.S. Cl. ........................................ 600/438; 73/573

(58) Field of Classification Search ......... 600/437–461; 604/19, 20, 601, 606; 73/597, 573
See application file for complete search history.

(56) References Cited

U.S. PATENT DOCUMENTS

| 4,422,332 A | * | 12/1983 | Dubuis et al. | .................. 73/625 |
| 5,099,848 A | | 3/1992 | Huang et al. | |
| 5,882,302 A | * | 3/1999 | Driscoll et al. | .............. 600/371 |
| 6,277,074 B1 | | 8/2001 | Zhu et al. | |

FOREIGN PATENT DOCUMENTS

| EP | 0 920 833 A | 6/1999 |
| WO | WO 00/55616 A | 9/2000 |

* cited by examiner

*Primary Examiner*—Long V Le
*Assistant Examiner*—Saurel J Selkin
(74) *Attorney, Agent, or Firm*—DLA Piper LLP (US)

(57) ABSTRACT

A device for measuring elasticity of a human or animal organ or viscoelastic media having an ultrasonic signal after ultrasonic illumination including at least one sensor including an ultrasonic transducer, at least one position sensor, an actuator to trigger the device connected by wire link to an electric power source, and a controlled electrodynamic actuator attached to the ultrasonic transducer that generates a transitory low-frequency impulse having a frequency range between about 1 Hz and about 5000 Hz.

27 Claims, 4 Drawing Sheets

DEVICE AND METHOD FOR MEASURING THE ELASTICITY OF A HUMAN OR ANIMAL ORGAN

RELATED APPLICATION

This is a continuation of International Application No. PCT/FR2003/002243, with an international filing date of Jul. 16, 2003 (WO 2004/016176, published Feb. 26, 2004), which is based on French Patent Application No. 02/10104, filed Aug. 8, 2002.

TECHNICAL FIELD

This disclosure pertains to a device and a method for measuring the elasticity of a human or animal organ or, more generally, all viscoelastic media having an ultrasonic signal after being subjected to ultrasonic impulses. Our disclosure applies particularly, but not exclusively, to measuring the elasticity of the liver of a human or an animal, the value of this measurement being that it correlates with the amount of fibrosis present in the liver.

BACKGROUND

Chronic hepatitis, which can be of alcoholic, viral or other origin, has a fibrotic effect that is important to evaluate to determine the best time to treat the hepatitis.

There do not exist on the market at present devices for measuring the elasticity that can be performed in a noninvasive manner, i.e., without collecting a portion of the organ or medium.

U.S. Pat. No. 5,882,302 is known in the prior art. It describes a transducer attached to a motor. The motor enables displacement of the transducer in a manner to obtain images of the different zones of the medium. The motor is thus used to modify the imaged zone and not for generating a low-frequency impulse. Moreover, the displacement in this context is not parallel to the axis of the ultrasonic beam.

Also known is U.S. Pat. No. 6,277,074 which describes a device in which displacement of the motor is also parallel to the ultrasonic axis. It does not disclose acquisition of the signals during compression. In fact, as in the case of U.S. Pat. No. 5,882,302, the motor is used to displace the transducer and not for generating a low-frequency impulse.

U.S. Pat. No. 5,099,848 discloses an ultrasonic device associated with a vibrator used in monochromatic mode of frequency fixed at 50 Hz. Moreover, in that device the transducer is not carried by the actuator and thus cannot be used for generating a low-frequency impulse.

With regard to the most recent devices for the study and analysis of the elasticity of a medium, WO 00/55616 describes an imaging method for observing the propagation of a low-frequency shear impulse wave simultaneously at a multitude of points of a diffusing viscoelastic medium. For this purpose there is emitted an ultrarapid cadence of ultrasonic compression waves which enable production of a succession of images of the medium. The images obtained in this manner are then processed by intercorrelation to determine at each point of each image the movements of the medium upon propagation of the shear wave. This device does not enable localization of the zone in which the elasticity is measured.

In available devices, when the ultrasonic transducer is used to generate a low frequency impulse by vibrating mechanically, the transducer is mobile and the reference frame is not fixed. One uses a technique that is well known by the expert in the field to compensate for this displacement. That solution has multiple drawbacks:

it uses an ultrasonic echo originating from a deep and immobile zone of the medium, it has low precision because the medium is not immobile, the form of the low-frequency impulse is poorly determined, it represents a supplementary algorithm that increases the calculation time, the surface of the medium presents a resistance to the applied shock, the real form of the low-frequency impulse, depends on the pressure applied by the operator.

In addition to the problems linked to the compensation of the displacement of the vibrator, the pressure exerted by the operator is a parameter that is not taken into account when it disturbs the measurement of elasticity.

Moreover, the study of shallow media with a system of the conventional type in direct contact can be difficult because the focal zone of certain transducers does not enable production of a clean ultrasonic signal at a short distance from the transducer.

In the measurement of conventional displacements implemented, e.g., by blood flows, the amplitude of the displacements is not linked to the depth in the medium, but to the phenomena observed, e.g., the displacements linked to the flow of blood are greater in the center of the artery than at its sides. The algorithm used to measure the displacements is thus the same irrespective of the depth. In contrast to elastography, the amplitude of the displacements depends on the distance which was given to the low-frequency vibration. When the vibration was given from the surface, the amplitude of the displacements generated by the low frequency impulse decreases as the wave penetrates deeply into the tissues. The use of a classic algorithm is not favorable for the measurements of the displacements over the entire range of depths.

SUMMARY

This disclosure relates to a device for measuring elasticity of a human or animal organ or viscoelastic media having an ultrasonic signal after ultrasonic illumination including at least one sensor including an ultrasonic transducer, at least one position sensor, an actuator to trigger the device connected by wire link to an electric power source, and a controlled electrodynamic actuator attached to the ultrasonic transducer that generates a transitory low-frequency impulse having a frequency range between about 1 Hz and about 5000 Hz.

This disclosure also relates to a method for calculating elasticity of a human or animal organ or viscoelastic media having an ultrasonic signal after ultrasonic illumination with a device including at least one ultrasonic transducer, at least one position sensor, a controlled electrodynamic actuator connected by wire link to an electric power source, including generating a low-frequency impulse and acquiring ultrasonic signals, compensating for relative displacement of the transducer, determining tissue velocities by using displacements between acquired signals in the organ/media, determining velocities of tissue deformations, determining velocity of the elastic wave, and determining the elasticity.

BRIEF DESCRIPTION OF THE DRAWINGS

Modes of execution of the disclosure will be described below as nonlimitative examples with reference to the attached figures in which.

DETAILED DESCRIPTION

Figure 1:
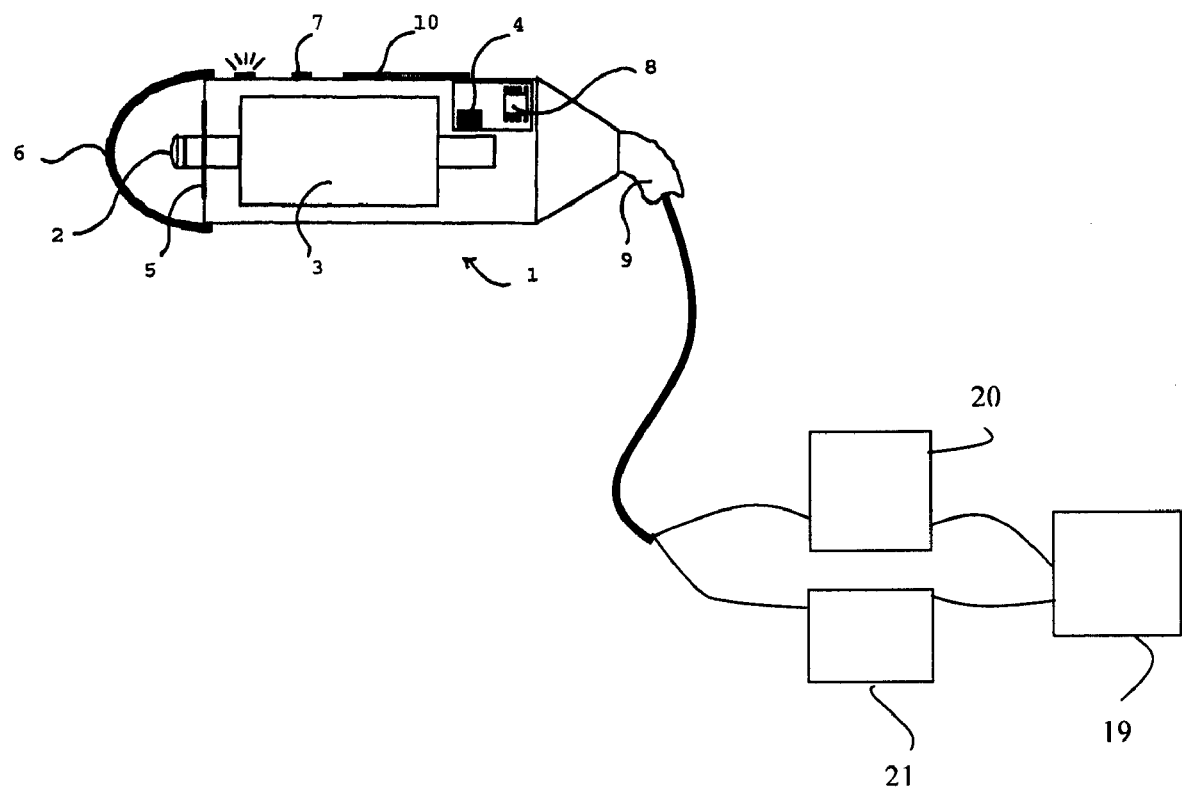
FIG. 1 illustrates an example of a device for measuring the elasticity of a human or animal organ.
Figure 1:
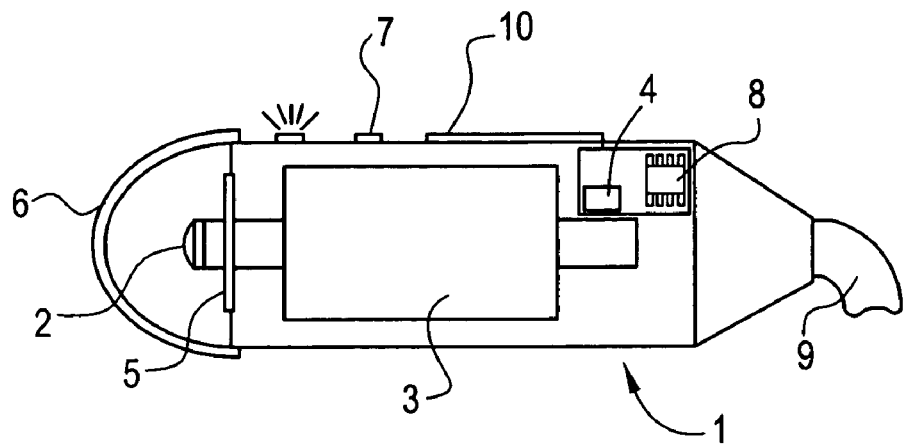

It will be appreciated that the following description is intended to refer to specific embodiments of the disclosure selected for illustration in the drawings and is not intended to define or limit the disclosure, other than in the appended claims.

This disclosure provides a device for measuring the elasticity of a human or animal organ, especially a liver, or more generally all viscoelastic media having an ultrasonic signal after being subjected to ultrasonic impulses, comprising at least one sensor comprising an ultrasonic transducer, at least one position sensor, an actuator for triggering the device, connected by wire link to an electric power source, and a controlled electrodynamic actuator attached to the ultrasonic transducer capable of generating a transitory low-frequency impulse having a frequency range comprised between about 1 Hz and about 5000 Hz.

The term "transitory low-frequency impulse" is understood to mean a mechanical stress of determined duration the frequency of which is comprised between about 1 Hz and about 5000 Hz and the peak-to-peak amplitude of which is comprised between about 10 μm and about 20 millimeters, preferably between about 500 μm and about 5 mm. The duration of this stress is comprised between about 100 μs and about 20 seconds, preferably between about 5 ms and about 40 ms (milliseconds).

We make it possible to provide a device which can produce a low-frequency vibration or stress that is perfectly controlled in time and amplitude. The knowledge of the exact displacement enables compensation under the best conditions and the relative displacement of the vibrator in a minimum of time. The form of the impulse is better controlled which enables more reliable measurements and thus an increase in the reproducibility of the system. By means of the use of the controlled electromagnetic actuator, also referred to as "controlled vibrator," the device has a reduced volume and weight. Lastly, the presence of a control loop provides better knowledge of the pressure applied by the operator.

The device comprises a protective device intended to protect the ultrasonic transducer.

The device is advantageously controlled by at least one controller, e.g., a computer, a microcomputer or a central processing unit. Similarly, the sensor comprises a flexible, watertight membrane.

The device for measuring the elasticity of a human or animal organ is associated with a control module and an ultrasound acquisition module capable of communicating with each other. The controller is capable of communicating with the control module and the ultrasound acquisition module.

The controller and the user interface are powered electrically by at least one battery.

This device advantageously comprises a user interface, e.g., a display screen connected to the control means. The device is associated with at least one echograph. The images and information obtained are displayed on a screen, ideally the screen of the echograph. The device can be fitted around an echographic bar. In the same manner, the echographic bar can itself implement the measurement of elasticity provided that it is equipped with a controlled vibrator system.

The device for the measurement of the elasticity of a human or animal organ may comprise an elastic intermediary medium transparent to ultrasounds and for the low-frequency wave such as, e.g., a synthetic polymer of the polyacrylamide type.

At least the end of the ultrasonic transducer advantageously has an elongated shape, e.g., an oblong, rectangular or ellipsoid shape with a length between about 2 and about 20 millimeters, preferably about 11 millimeters, and a width between about 1 and about 10 millimeters, preferably about 5 millimeters.

The ultrasonic transducer can advantageously have a conical or tapered shape with an angle between about 10 and about 80 degrees.

The disclosure also pertains to a method for calculating an elasticity by means of the device, comprising the following steps:

possible localization by image mode of the desired zone, the acquisition of the ultrasonic signals, i.e., for the echo lines, can take place at a cadence of about 50 lines per second,
  generation of the low-frequency impulse and acquisition of the ultrasonic signals; the acquisition for the measurement of the elasticity being performed at a high cadence between about 100 Hz and about 100,000 Hz,
  compensation of the relative displacement of the vibrator, calculation of the tissue velocities, i.e., the displacements between the acquisitions, in the medium,
  calculation of the velocities of the tissue deformations,
  calculation of the velocity of the elastic wave, and
  calculation of the elasticity.

The method advantageously comprises a prior step of localization by image mode of the desired zone, the acquisition of the ultrasonic signals, i.e., for the echo lines, taking place, e.g., at a cadence of about 50 lines per second. The result obtained by the step of calculation of the elasticity is superposed on the echo lines, e.g., in the form of a level of different color.

The method advantageously comprises a step of automatic recognition of the organ examined/studied by the calculation of tissue parameters such as, e.g., the coefficient of ultrasonic retrodiffusion. The automatic recognition is based on the calculation of tissue parameters of the organ under study and on the comparison of these parameters with the values presented in the literature. As an example, the tissue parameter can be the coefficient of ultrasonic retrodiffusion measured in real time from the echo lines.

The low-frequency impulse or signal advantageously has a frequency between about 1 Hz and about 5000 Hz and a duration ranging from about 1/2f to about 20/f.

According to an example selected to illustrate aspects of the disclosure and illustrated in FIG. 1, the device comprises a sensor 1 comprising at least one ultrasonic transducer 2, an electrodynamic actuator 3, an ultrasonic transducer, a flexible watertight membrane 5, a protective cap 6, a push-button 7 for triggering the device, the electronic equipment 8 of the ultrasonic transducer, a cable 9 and an alphanumeric display screen 10.

The sensor 1 is controlled by a controller constituted in FIG. 1 by a microcomputer or by a central processing unit, not shown in the various figures, which can, e.g., be a card loaded in a case linked by a flexible cable to the sensor 1. A display screen, also referred to as "user interface," allows the user or operator to read the information provided by the system.

A control module and an ultrasound acquisition module, neither of which is shown in the attached figures, are both connected to the sensor 1. The two modules communicate together. The acquisition module sends a synchronization signal at the moment in which an ultrasound acquisition is triggered. The corresponding position is then recorded in a manner such that it can be communicated to a compensation algorithm. The central processing unit communicates with the ultrasound acquisition module and the control module. The user interface is constituted of a screen that is optionally a touch screen, a keyboard and optionally cursors.

The image of the medium to be measured can be displayed on the screen to assist the user in localizing the zone in which he wants to perform the elasticity measurement. The ultrasonic transducer is then used in standard echographic mode in a manner to acquire typically 50 ultrasonic lines per second of the medium. The envelope of these ultrasonic lines is displayed on the screen. The lines are coded in gray level and in logarithmic scale and placed side by side to constitute an image. The sensor 1 can be equipped with a positioning system to know the positions at which the lines are acquired and thereby reconstitute the image of the medium to be measured when the user, practitioner or operator slides the sensor 1 on the surface of the human or animal tissues.

We describe below the steps of the method for obtaining the elasticity measurement with the succession of these steps being defined according to the order below:
1) possible localization by image mode of the desired zone, the acquisition of the ultrasound signals, i.e., for the echo lines, can take place at a cadence of about 50 lines per second;
2) generation of a low-frequency impulse and acquisition of the ultrasonic signals; the acquisition for the measurement of the elasticity being performed at a high cadence between about 100 Hz and about 100,000 Hz;
3) compensation of the relative displacement of the vibrator;
4) calculation of the tissue velocities, i.e., the displacements between the acquisitions in the medium;
5) calculation of the velocities of the tissue deformation;
6) calculation of the velocity of the elastic wave; and
7) calculation of the elasticity.

In the framework of the generation of the low-frequency impulse and the ultrasound acquisition, N ultrasound acquisitions are implemented at a cadence 1/T typically between about 100 Hz and about 10,000 Hz. Essentially at the same instant, a low-frequency signal is transmitted to the vibrator system, preferably just after the beginning of the ultrasound acquisitions. This signal has a frequency f between about 5 Hz and about 1000 Hz and a duration ranging from about 1/2f to about 20/f. The low-frequency vibration leads to the propagation in the tissues of an elastic wave the velocity of which depends on the elasticity of the medium.

The acquisition of the ultrasonic data is performed by emitting with the ultrasonic transducer 2 an ultrasonic impulse which is reflected by the particles contained in the medium. The ultrasound signal called "speckle" is recorded by the same ultrasonic transducer 2 over a duration that can range between about 1 µs and about 10 ms. This operation is repeated a number N of times at the cadence 1/T.

The transducer is fixed on the vibrator or the controlled actuator or, to the contrary, the actuator is fixed on the transducer.

In the step of compensation of the relative displacement of the vibrator, the displacement of the sections of tissue between two ultrasonic acquisitions, d(z,t), is measured in relation to the position of the transducer. When the transducer is immobile, the displacements measured experimentally are substantially equal to the absolute displacements. In contrast, when the transducer is used to generate the low-frequency wave, it is necessary to take into account the displacement of the transducer because the displacements measured experimentally are no longer equal to the absolute displacements. The displacement of the vibrator must be subtracted from the measured displacements to obtain the absolute displacements. The displacements measured relative to the transducer are expressed by:

$$d(z,t) = \delta(z,t) - D(t)$$

in which z is the depth, D(t) is the absolute displacement of the vibrator and $\delta(z,t)$ is the absolute displacement of the section of the medium located at the depth z. The vibrator is placed at the depth z=0.

Moreover, since the displacements are derived in relation to the depth to obtain the deformations, the noise can become considerable. And, in fact, the derivation is very sensitive to noise. It thus appears important to compensate under good conditions the displacement of the vibrator. The presence of a position sensor 4 enables reliable direct measurement of D(t). The compensation (or readjustment) of the ultrasonic lines can, for example, be performed in Fourier's domain.

The discrete Fourier transform of the ultrasound line number m acquired at the time t=mT is $$\sum_{n=0}^{N-1} r(m,n) \exp\left(-j \frac{2\pi nk}{N}\right)$$

in which r(m,n) is the sampled signal, N is the number of samples. If the ultrasound line a was acquired at the time t=mT then the compensated line $r_s(m,n)$ is expressed in the temporal domain by $$r_s(m,n) = \sum_{n=0}^{N-1} R(m,k) \exp\left(j \frac{2\pi k}{N}\left(n + \frac{2D(t)}{cT_s}\right)\right).$$

In the step of calculation of the tissue velocities, the displacements are measured either by intercorrelation, by Doppler or by autocorrelation and more generally by any other displacement measurement technique. As an example, it is possible to use the autocorrelation algorithm described by Kasai:

$$\delta(z, t = mT) = \frac{V_c}{4\pi f_c} \arg\left(\sum_{n=p-m}^{n=p+m} \bar{r}_s(m, n)\bar{r}_s*(m+1, n)\right)$$

in which $\bar{r}_s$ is the Hilbert transform of $r_s \cdot r_s^*$ is the conjugate of $\bar{r}_s$. With this algorithm, it is possible to measure the displacement $\delta(z,t)$ of the section of tissue located between the depths $(p-m)\Delta 2$ and $(p+m)\Delta 2$ between the times $mT$ and $(m+1)T$ in which $T$ is the period between two successive ultrasonic blasts and $\Delta z$ the pace of spatial sampling in depth. The tissue velocity $v(z,t)$ is expressed by $$v(z,t) = \delta(z,t)/T$$

In the step of calculating the velocities of tissue deformation, the velocity of tissue deformation is obtained by deriving $v(z,t)$ in relation to the depth:

$$\varepsilon(z, t) = \frac{\partial v(z, t)}{\partial z}.$$

In the step of calculating the velocity of the elastic wave, the measurement of the velocity of the elastic wave is, as an example, obtained by calculating the phase $\phi(z)$ of the shear wave at the central frequency fo of the elastic wave at each depth in the medium:

$$\varepsilon'(z, f) = FT(\varepsilon(z, t))$$
$$\varphi(z) = \arg(\varepsilon'(z, f_o))$$
$$V_s(z) = \frac{2\pi}{f_o}\left(\frac{d\varphi(z)}{dz}\right)^{-1}.$$

In the step of calculating the elasticity, in soft media such as biological tissues and more generally solid media principally constituted by water in liquid form, the elasticity (Young's module) is expressed as a function of the shear velocity which we will indicate as $V_s$ and the density $\rho$:

$$E = 3\rho V_s^2$$
$$E(z) = 3\rho\left[\frac{2\pi}{f_o}\left(\frac{d\varphi(z)}{dz}\right)^{-1}\right]^2.$$

Thus, the device for measuring the elasticity of a human or animal organ yields either a mean value of the elasticity between two depths indicated by the user or the variations of the elasticity as a function of the depth.

According to one aspect, the sensor 1 can comprise multiple transducers which can be positioned in an arbitrary manner, e.g., linearly (like an echographic rod) or in a honeycomb pattern. In this manner, the elasticity can be measured in different zones of the medium to be analyzed.

Outside of the acquisition periods, the device acquires ultrasound lines at a typical cadence of about 50 lines per second. These lines are processed like a standard echograph in a manner to conserve the envelope of the signal. The lines are then displayed on the screen of the device in gray level and in logarithmic scale each following the others and each next to the others so as to form an image.

The image can be obtained by displaying at roughly constant velocity the sensor 1 at the surface of the liver, the user then having available a deformed image of the observed zone. The image is deformed because it is not possible for the user to displace the sensor 1 at constant velocity. This image allows the user to determine the zone in which the measurement is performed. The deformation of the image is markedly reduced by measuring the position of the sensor 1 at the surface of the medium. The lines are displayed on the screen as a function of the abscissa of the sensor on the medium.

Figure 2:
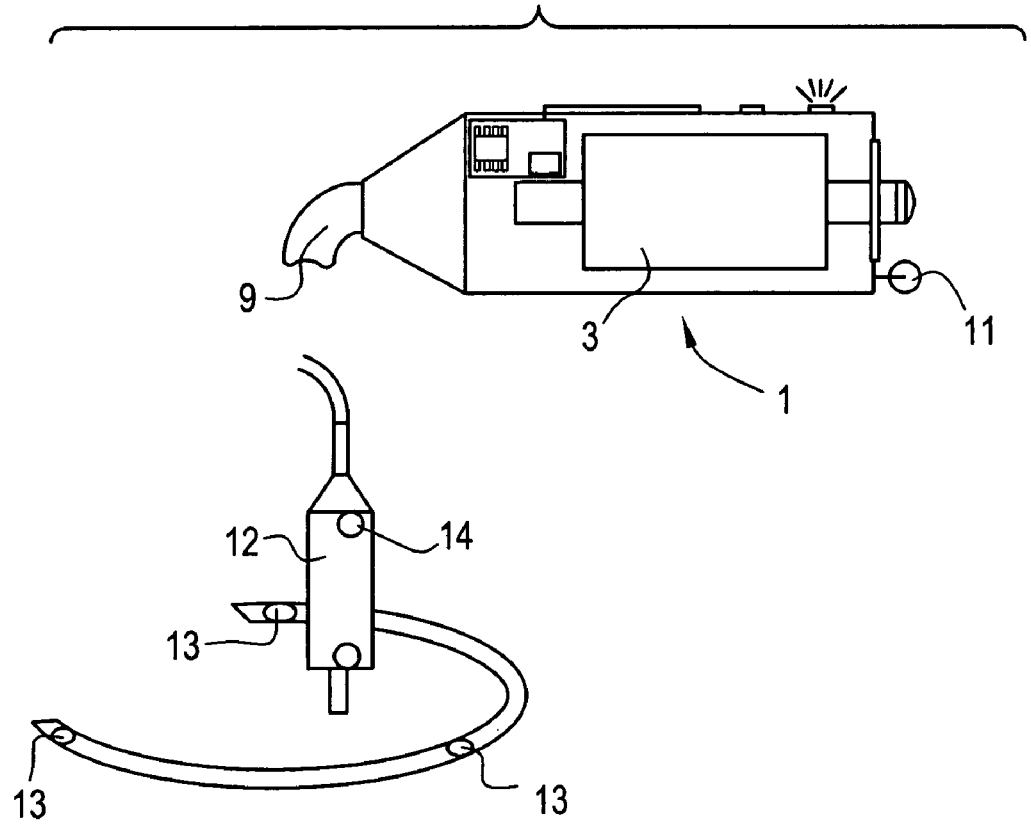
FIG. 2 illustrates said device equipped with a wheel and a means of low-frequency ultrasonic positioning constituted by at least three ultrasonic receivers.
Figure 3:
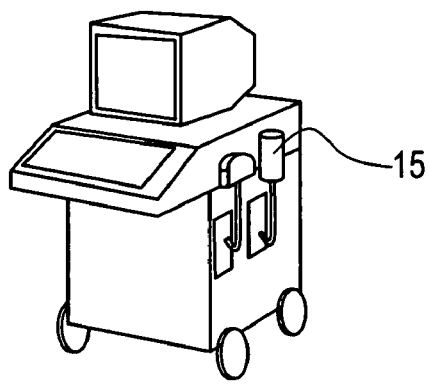
FIG. 3 illustrates a device associated with an echograph.

As illustrated in FIG. 2, the position of the sensor 1 on the surface of the medium can be obtained with the aid of a measurement system that can be of different types:

position sensor of the type used in microcomputer mice; it is then possible to select a system using a wheel 11, an optical system like those used for optical mice;

low-frequency ultrasonic positioning system 12 (typically 100 kHz) constituted by at least three ultrasonic receivers 13 arranged on the body of the patient and at least one transmitter 14 placed on the sensor (the position is obtained by triangulation);

or any other system for the measurement of displacement; the system being connected to the central processing unit.

The device for the measurement of the elasticity of a human or animal organ can be associated with a standard echograph 15. In this manner the echograph not only provides morphological information on the organs, but also a quantitative elasticity parameter.

Figure 4:
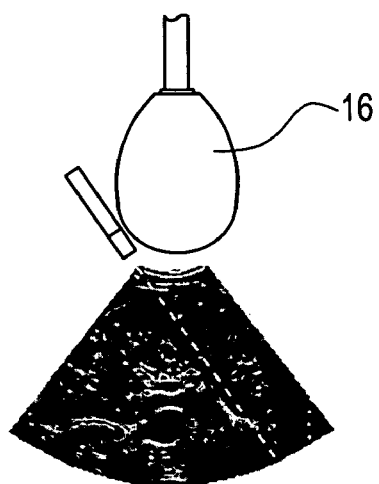
FIG. 4 illustrates the device represented in FIG. 3 associated with the sensor which is placed on the side of an echographic bar for obtaining the image of the liver and thereby localized the analyzed zones.
Figure 5A:
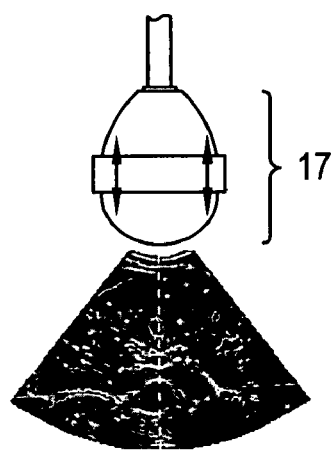
FIGS. 5a to 5d illustrate the measurements of elasticity superposed on the echographic image in the case in which the device is associated with an echograph, the echographic sensor being superposed on the echographic image.

1. The echograph can then have in addition to the standard echographic sensors 16, a sensor of the tracer type 17 as illustrated in FIG. 5*a*. The sensor 17 can be fitted around an echographic bar, not shown in the figures, in the manner of certain guiding systems for biopsies or old continuous Doppler systems as illustrated in FIG. 4.
2. It can also be envisioned that the ultrasonic bar itself performs the acquisition of the ultrasonic signals used for the elastography algorithm.

Our device can advantageously be portable whether it be plugged in to the power grid or powered by batteries. A scanning for the measurement of the elasticity can be performed manually to obtain an image of the elasticity. In the same manner, the scanning can be performed by means of a step motor or any other type of controlled electromagnetic actuators.

Figure 5B:
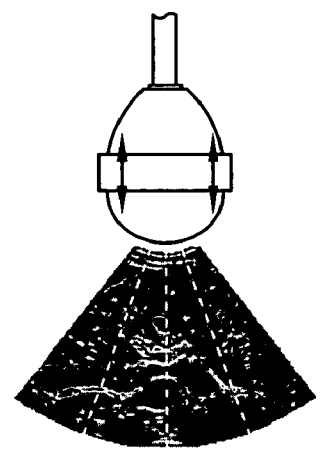
Figure 5C:
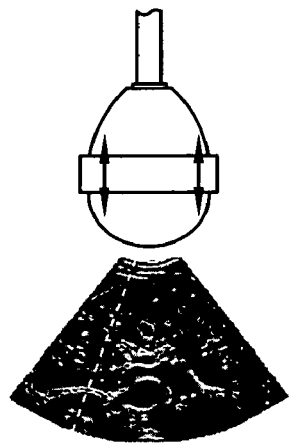
Figure 5D:
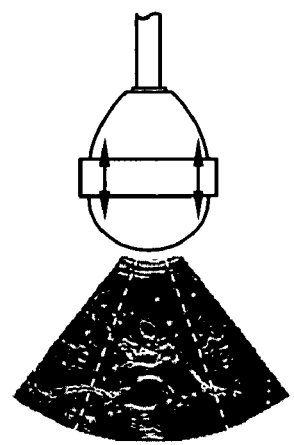
Figure 6:
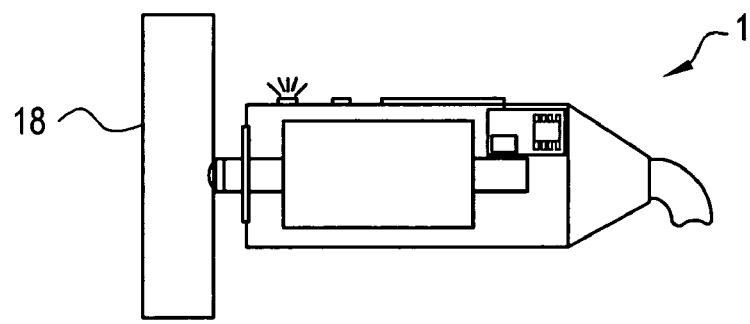
FIG. 6 illustrates a device with an elastic intermediary medium transparent to ultrasounds.
Figure 7A:
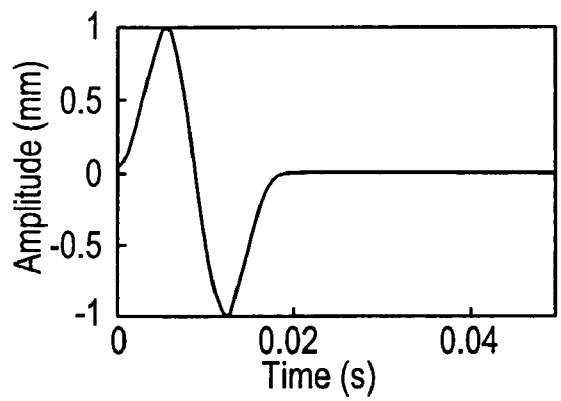
FIGS. 7a and 7b illustrate respectively the shape of a low-frequency impulse of peak-to-peak amplitude of 2 millimeters and the frequency spectrum of the low-frequency impulse the central frequency of which is 50 Hz and the bandwidth of which at half height extends from 18 Hz to 100 Hz, the pass band reaching 82 Hz at −6 dB (decibels).
Figure 7B:
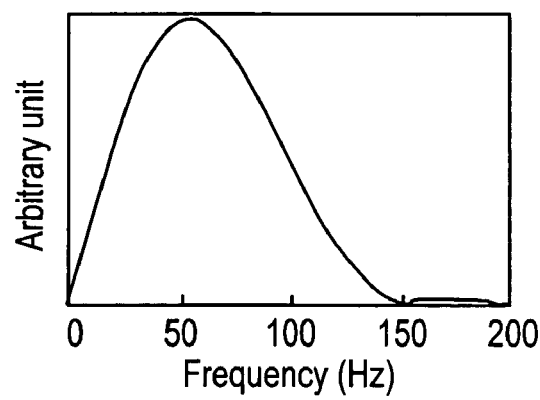

The system can optionally share the electronic modules of the echograph 15 because the standard echographs 15 are a priori equipped with signal processing units capable of running or calculating the algorithms required for measuring the elasticity. The bar itself can then optionally generate the low-frequency impulse by a vibration movement which can be perpendicular to the surface of the medium. The acquisition can be performed on the central line of the echographic image as illustrated in FIG. 5*a*. It is possible to change the acquisition line and reproduce the low-frequency impulse in a manner so as to scan the entire surface of the image as illustrated in FIGS. 5*b* to 5*d*. It is possible to create multiple lines at the same time using evolved ultrasonic focusing techniques such as:

the method described by Shattuck (cf. "A parallel processing technique for high speed ultrasound imaging with linear phased arrays", J. Acoust. Soc. Am. 75(4), 1273-1282, 1984), a comb type technique as represented in FIGS. 5*b* to 5*d* in which 2, 4 or even 8 lines are acquired simultaneously. In the example of FIG. 5*d*, the lines i and i+64 are obtained at the same time.

a technique of formation of ultrarapid paths using a summation-retard algorithm like the one described in FR 9903157, of other types of beam forming like, e.g., the technique of spatial frequencies in space.

This device can be used conjointly with the ultrarapid imaging techniques described in the previously cited documents in a manner to obtain an image of the elasticity.

According to one aspect, the device uses an elastic intermediary medium 18 transparent to ultrasound. This medium 18 can be, e.g., a synthetic polymer of the polyacrylamide type. An adhesive material or a glue can be placed between the intermediary medium 18 and the medium under study in a manner to obtain either a sliding interface or a linked interface. The intermediary medium 18 is innovative because it is not only transparent for ultrasound, but also for low-frequency waves. The intermediary medium 18 is selected in a manner so as to present an elasticity close to that of the medium under study in a manner to adjust the impedance and thereby enable a maximum of energy to be transmitted to the medium under study. The intermediary medium 18 can also be compressed such that its module of elasticity which varies in a nonlinear manner becomes close to that of the medium under study. This last proposition is moreover an original technique for measuring the elasticity of the medium: it comprises modifying the elasticity of the intermediary medium 18 until a maximum of energy is transmitted. The elasticity attained is then close to that of the medium.

The device and method moreover have available an algorithm or means for calculating the displacements which is adjusted as a function of the depth in the medium. At a shallow depth, where the amplitude of the displacements is large, the algorithm compares the successive lines with each other. In contrast, at deep depths, when the amplitude of the displacements between successive lines is small, the correlation is effected between the line m and the line m+Δ with Δ>1. By jumping multiple lines in this manner, the amplitude of the displacement to be measured increases and the signal to noise ratio is augmented. Adaptation of Kasai's algorithm yields $$\delta(z, t = mT) = \frac{V_c}{4\pi f_c} \arg\left(\sum_{n=p-m}^{n=p+m} \bar{r}_s(m, n)\bar{r}_s * (m + \Delta(z), n)\right)$$

in which Δ(z) is a whole number such that Δ(z)≧1 which increases with U(z,t)=depth.

Knowledge of the effects of diffraction associated with the vibrator used in an isotropic or anisotropic medium makes it possible to compensate perfectly the effects of diffraction. It is also possible to estimate the attenuation in the medium. In the case of a source of low-frequency pressure in disk form, the impulse response of diffraction on the axis follows the following equation:

$$\begin{cases} \frac{2aR^2 t}{\rho(z^2+R^2)^{3/2}}, & si\, O \leq t \left(\frac{\sqrt{z^2+R^2}}{V_s}\right) \\ O, & si\, \frac{\sqrt{z^2+R^2}}{V_s} \leq t \end{cases}$$

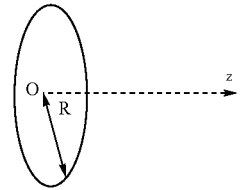

in which z is the depth on the axis of the disk, ρ is the density of the medium, u is the displacement along the axis of symmetry Oz associated with a stress a applied along Oz, t=the time, R is the radius of the disk and $V_s$ is the shear velocity. It is possible to introduce the attenuation α into this equation. This equation contains both the effects of diffraction and of coupling. An estimation of $V_s$ or of α can be obtained by calculation. As an example, it is possible to use an iterative calculation of optimization which comprises minimizing the cost function which is the module of the difference between the deformations measured experimentally and those obtained with the theoretical model.

The diclosure was described above as an example. It is understood that one skilled in the art can implement different variations of the device and the method for measuring the elasticity of a human or animal organ, in particular with regard to the arrangement or fittings of the different elements constituting the device or the order as well as the importance of the steps of the method without going beyond the scope of the patent as defined in the appended claims.

The invention claimed is:

1. A device for measuring elasticity of a human or animal organ or viscoelastic media having an ultrasonic signal after being subjected to ultrasonic impulses comprising:
   at least one sensor comprising an ultrasonic transducer,
   at least one position sensor,
   an actuator to trigger the device connected by wire link to an electric power source,
   a controlled electrodynamic actuator attached to the ultrasonic transducer that generates a transitory low-frequency impulse having a frequency range between about 1 Hz and about 5000 Hz and results in a low-frequency vibration or stress that is controlled in time and amplitude and allows an operator to apply pressure to the organ, and
   a computer configured to calculate velocities of tissue deformations.

2. The device according to claim 1, further comprising at least one controller connected to the sensor.

3. The device according to claim 2, wherein the controller is selected from the group consisting of a computer, a microcomputer and a central processing unit.

4. The device according to claim 1, wherein the sensor comprises a flexible, watertight membrane.

5. The device according to claim 1, wherein the sensor comprises a protective device that protects the ultrasonic transducer.

6. The device according to claim 1, wherein the sensor connects to a control module and an ultrasound acquisition module that communicate with each other.

7. The device according to claim 2, wherein the controller communicates with the control module and the ultrasound acquisition module.

8. The device according to claim 2, further comprising a user interface connected to the controller.

9. The device according to claim 1, wherein the sensor connects to at least one echograph that displays obtained images on a screen.

10. The device according to claim 9, wherein the electrograph further comprises an echographic bar and the bar implements acquisition of ultrasound signals.

11. The device according to claim 1, further comprising at least three receivers for arrangement on a body of a patient and at least one transmitter placed on the sensor.

12. A device for measuring elasticity of a human or animal organ or viscoelastic media having an ultrasonic signal after being subjected to ultrasonic impulses comprising:
at least one sensor comprising an ultrasonic transducer,
at least one position sensor,
an actuator to trigger the device connected by wire link to an electric power source, and
a controlled electrodynamic actuator attached to the ultrasonic transducer that generates a transitory low-frequency impulse having a frequency range between about 1 Hz and about 5000 Hz, and further comprising an elastic intermediary medium adjacent to the transducer and transparent to ultrasound and the low-frequency impulse.

13. The device according to claim 12, wherein the intermediary medium has an elasticity close to that of a medium being measured by compressing the intermediary medium in a manner to vary its modulus of elasticity.

14. The device according to claim 8, wherein the controller and the user interface are electrically powered by at least one battery.

15. The device according to claim 1, further comprising a device for calculating displacements connected to the sensor which is adapted as a function of the depth of the human or animal organ.

16. The device according to claim 1, wherein at least an end of ultrasonic transducer has an elongated shape, and has a length between about 2 and about 20 millimeters, and a width between about 1 and about 10 millimeters.

17. The device according to claim 1, wherein the ultrasonic transducer has a conical or tapered form having an angle between about 10 and about 80 degrees.

18. A method for determining elasticity of a human or animal organ or viscoelastic media having an ultrasonic signal after being subjected to ultrasonic impulses with a device comprising at least one ultrasonic transducer, at least one position sensor, a controlled electrodynamic actuator connected by wire link to an electric power source, comprising:
generating a low-frequency impulse with the ultrasonic transducer and acquiring ultrasonic signals with the ultrasonic transducer,
compensating for relative displacement of the transducer,
determining tissue velocities by using displacements between acquired signals in the organ/media,
determining velocities of tissue deformations,
determining velocity of the elastic wave, and
determining the elasticity according to $E=3pV_s^2$, wherein E is elasticity, p is density of the organ and $V_s$ is velocity of the elastic wave.

19. The method according to claim 18, further comprising a prior step of localization by image mode of a desired zone, and wherein acquisition of the ultrasound signals takes place at a selected cadence of about 50 lines per second.

20. The method according to claim 19, wherein results obtained from determining the elasticity is superposed on the ultrasound signals in the form of a level of different color.

21. The method according to claim 18, wherein the low-frequency impulse has a frequency between about 1 Hz and about 5000 Hz and a duration ranging from about 1/2f to about 20/f.

22. The method according to claim 18, wherein determining the tissue velocity is implemented by intercorrelation, by Doppler, by autocorrelation or a technique for measurement of displacements.

23. The method according to claim 18, wherein determining the velocity of tissue deformation is performed by deriving the tissue velocity by depth.

24. The method according to claim 18, wherein the acquisition of signals is performed at a cadence between about 100 Hz and about 100,000 Hz.

25. The method according to claim 18, further comprising a prior step of scanning the human or animal organ manually or using a step motor or controlled electromagnetic actuators.

26. The method according to claim 18, further comprising a step of automatic recognition of the medium by calculating the coefficient of ultrasonic retrodiffusion.

27. The device according to claim 6, wherein a controller communicates with the control module and the ultrasound acquisition module.

* * * * *